United States Patent

Ogama

Patent Number: 6,044,286
Date of Patent: Mar. 28, 2000

[54] SKIN-CONTACT TYPE MEDICAL TREATMENT APPARATUS

[75] Inventor: Kenji Ogama, Tokyo, Japan

[73] Assignee: Kabushiki Kaisha Bangahdo, Tokyo, Japan

[21] Appl. No.: 09/115,606

[22] Filed: Jul. 15, 1998

[30] Foreign Application Priority Data

Jul. 31, 1997 [JP] Japan .................................. 9-206525
Jun. 17, 1998 [JP] Japan ................................. 10-169530

[51] Int. Cl.[7] .................................................. A61N 1/04
[52] U.S. Cl. .......................... 600/372; 600/393; 607/115; 607/152
[58] Field of Search ............................ 607/1, 2, 75, 115, 607/142, 152; 600/372, 382, 393, 395

[56] References Cited

U.S. PATENT DOCUMENTS

| | | | |
|---|---|---|---|
| 4,448,199 | 5/1984 | Schmid | 600/393 |
| 5,312,326 | 5/1994 | Myers et al. | 607/152 |
| 5,772,688 | 6/1998 | Muroki | 607/1 |
| 5,848,985 | 12/1998 | Muroki | 607/152 |

FOREIGN PATENT DOCUMENTS

| | | | |
|---|---|---|---|
| 61-55979 | 11/1986 | Japan . | |
| 61-55980 | 11/1986 | Japan . | |
| 62-32944 | 7/1987 | Japan . | |
| 3-50927 | 10/1991 | Japan . | |
| 4075669 | 3/1992 | Japan | 607/115 |
| 8-173554 | 7/1996 | Japan . | |
| 8100964 | 4/1981 | WIPO | 607/152 |

*Primary Examiner*—William E. Kamm
*Assistant Examiner*—Carl H. Layno
*Attorney, Agent, or Firm*—Kanesaka & Takeuchi

[57] ABSTRACT

A skin-contact type medical treatment apparatus includes a first element serving as a positive electrode and a second element serving as a negative electrode, which are electrically connected to each other through a resistance element when being in contact with the skin. The first and second elements are opposed to each other across the resistance element so as to be connected to the terminal ends of resistance element. The first and second elements and resistance element are formed flat on a substrate formed of a membrane of ceramic and placed in a fitting concave formed in a pedestal of synthetic resin.

19 Claims, 3 Drawing Sheets

SKIN-CONTACT TYPE MEDICAL TREATMENT APPARATUS

BACKGROUND OF THE INVENTION

1. Field of the Invention

This invention relates to a medical treatment apparatus to be attached to the skin for regaining health, and more particularly to a skin-contact type medical treatment apparatus effective in the treatment of unidentified complaint syndrome such as muscular stiffness.

2. Description of the Prior Art

As a domestic treatment apparatus for alleviating muscular stiffness or aches of the shoulders or other parts of the body, there have so far been proposed ion-permeating devices for curing muscular or nervous fatigue by imparting, to the skin, electric stimulation brought about by electromotive force generated by a biogalvanic battery formed with the application of a weak direct current to the body (cf. Japanese Patent Publication Gazettes Nos. SHO 61-55979, SHO 61-55980 and SHO 62-32944, and Japanese Utility Model Publication Gazette No. 3-50927).

The ion-permeating device described above is used in such a manner that a semiconducting crystal electrode and a metal electrode higher in standard single-electrode potential than the semiconducting crystal electrode are electrically connected to each other and brought into contact with the skin. The ion-permeating device enables muscular and nervous tissues to be continuously stimulated with electromotive force stably imparted to the skin through the electrodes without embrittling the electrodes during prolonged use. The ion-permeating device can achieve remarkably practical effects of treating the stiffness and aches in the body parts.

It seems that the function of alleviating such stiffness and aches in the body is fulfilled by electric stimulation caused by the biogalvanic battery. Thus, it is obvious that the medical effect of the ion-permeating device can be increased by enlarging the current from the biogalvanic battery.

However, when the muscular and nervous tissues are physiologically activated by the biogalvanic battery, impedance in the skin between the electrodes of the biogalvanic battery is remarkably decreased. As a result, the current flowing in the skin is increased in quantity to impart an excessive stimulation to the skin tissues, thus possibly suffering skin damages.

For solving such a problem, there is proposed a skin-contact type medical treatment apparatus as shown in FIG. 6, in which a first element 11 serving as a metal positive electrode and a second element 12 serving as a semiconductor negative electrode are electrically connected through a protective resistance element 13 (Japanese Patent Appln. Public Disclosure No. HEI 8-173554(A)).

Now, the prior art skin-contact type medical treatment apparatus mentioned above will described in further detail with reference to FIG. 6.

The first element 11 which is provided at its center with a protrusion is formed by plating a disk of copper with gold. This first element functions as a positive electrode of the biogalvanic battery when being in contact with the skin. The second element 12 is made by oxidizing the surface of a zinc annular plate having a center hole so as form an n-type semiconductor of zinc oxide. This second element functions as a negative electrode when being in contact with the skin. The protective resistance element 13 is made in such a manner that epoxy synthetic resin having carbon powder dispersed therein is uniformly applied to the surface (upper side in FIG. 6) of the first element 11 and dried to be formed into a resistance membrane. The protective resistance element 13 is adhered to the upper surface of the second element 12. An external circuit acting as the biogalvanic battery of the skin-contact type medical treatment apparatus is electrically connected to the protective resistance element 13. In the drawing, reference numeral 17 denotes adhesive cloth, and 18 denotes the skin.

Next, a method of producing the skin-contact type medical treatment apparatus will be explained.

First, the epoxy synthetic resin as the ingredient of the protective resistance element 13 is uniformly applied to the flat upper surface of the disk-shaped first element 11, and then, the second element 12 is placed on the flat upper surface of the first element before the epoxy synthetic resin becomes completely dry. Consequently, the first element 11 and second element 12 are superposed upon each other with the protective resistance element 13 interposed therebetween, with the center protrusion of the first element protruding upward through the center hole in the second element.

While the conventional skin-contact type medical treatment apparatus as shown in FIG. 6 brings about the intended effect of treating unidentified complaint syndrome such as shoulder or muscular stiffness and lumbago, it is necessary to uniformly apply epoxy synthetic resin to form the protective resistance element in the manufacturing process. The work of producing the conventional apparatus requires not only much skills in uniformly applying the epoxy synthetic resin, but also much time and labor. Furthermore, the conventional apparatus is disadvantageous in that the method of manufacturing the apparatus becomes complicated, because of the processes of putting the second element on the first element and then drying the epoxy synthetic resin applied to the first element. Accordingly, the conventional apparatus entails the aforenoted serious problems so that the medical treatment apparatus can be mass-produced uniformly in quality at a low cost with high efficiency.

OBJECT OF THE INVENTION

An object of the present invention is to provide a skin-contact type medical treatment apparatus which is capable of being mass-produced uniformly in quality and at a low cost.

SUMMARY OF THE INVENTION

To attain the object described above according to the present invention, there is provided a skin-contact type medical treatment apparatus comprising a first element of metal, which serves as a positive electrode, and a second element of n-type semiconductor, which serves as a negative electrode. The first element and second element are electrically connected to each other through a conductive element. The first and second elements and the conductive element are formed flat on the upper surface of a pedestal of an insulating material. The conductive element may be made of a material having an arbitrary resistance or a resistance of zero. The resistance of the conductive element may be determined within the range of 0 ohms to an arbitrary value when being produced so as to have a current limiting function.

The pedestal is provided in its upper surface with a fitting concave in which the first and second elements and conductive element are disposed flat, thereby to stabilize the first and second elements and conductive element. The formation of the first and second elements and conductive element on the upper surface of the insulating substrate facilitates the intimate integration of these elements. Furthermore, the formation of the fitting concave in the upper surface of the pedestal ensures the stability of positioning the substrate to be held in the fitting concave.

Since the works of coating and drying synthetic resin for forming the protective resistance element as noted above are not required for manufacturing the medical treatment apparatus of the present invention, the manufacturing process for the medical treatment apparatus can be simplified and carried out easily without requiring special skills. Consequently, the apparatus of the invention can be easily and speedily assembled and produced at a low cost and uniformly in quality with high efficiency.

Other and further objects of this invention will become obvious upon an understanding of the illustrative embodiments about to be described or will be indicated in the appended claims, and various advantages not referred to herein will occur to one skilled in the art upon employment of the invention in practice.

DESCRIPTION OF THE PREFERRED EMBODIMENTS

Figure 1:
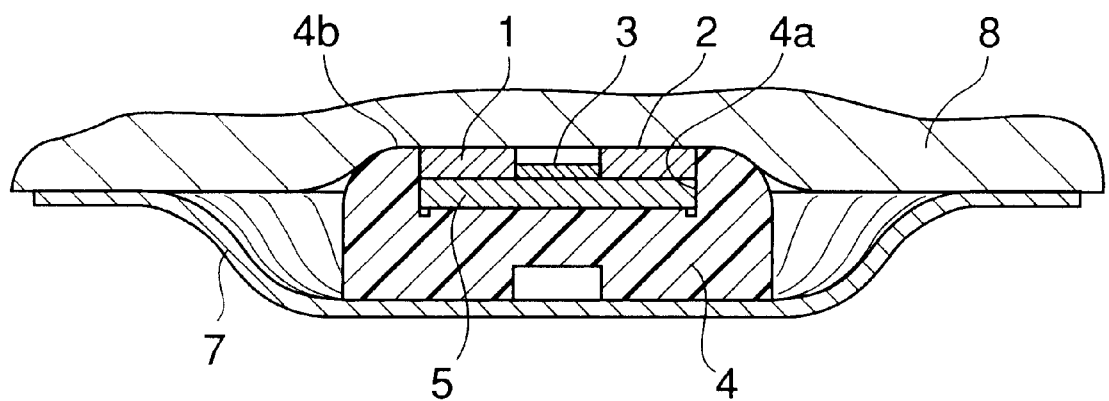
FIG. 1 is a sectional view showing a skin-contact type medical treatment apparatus in use according to this invention.
Figure 2:
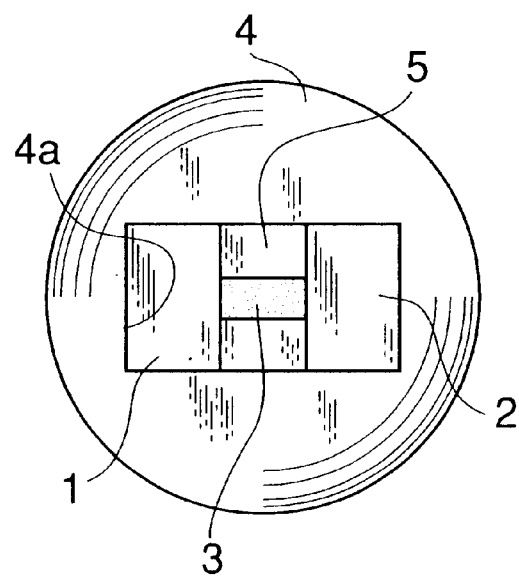
FIG. 2 is a plan view showing the skin-contact type medical treatment apparatus of this invention.
Figure 3:
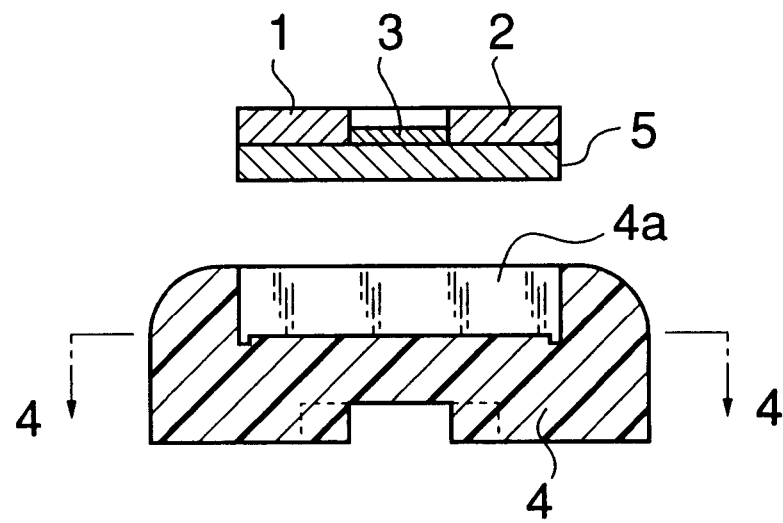
FIG. 3 is a sectional view showing the medical treatment apparatus of the invention in the exploded state.
Figure 4:
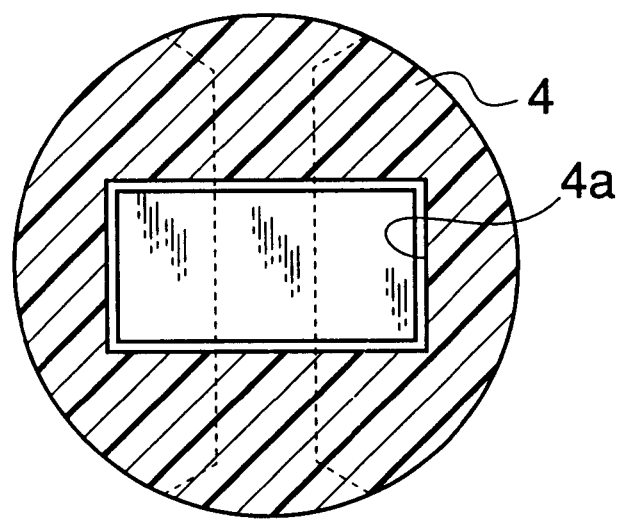
FIG. 4 is a sectional view taken along line 4—4 in FIG. 3.

One embodiment of the skin-contact type medical treatment apparatus according to the present invention will be described hereinafter with reference to FIG. 1 through FIG. 4.

The skin-contact type medical treatment apparatus comprises a first element 1, a second element 2, a conductive element (resistance element in this embodiment) 3 through which the first and second elements are connected to each other, and a pedestal 4. The first element 1, second element 2 and the resistance element 3 are formed flat on the upper surface of the pedestal 4.

The first element 1, second element 2 and the resistance element 3 are formed in the shape of a membrane on an insulating substrate 5 such as a ceramic plate, so as to be integrally united with the substrate.

The first element 1 is made of a conductive metallic material such as noble metals and constitutes a positive electrode of a biogalvanic battery when being into contact with the skin. The first element 1 in the illustrated embodiment is an electrically conductive element consisting of a coating film which is formed by baking gold paste onto the substrate 5.

The second element 2 is made of n-type semiconductor and constitutes a negative electrode of the biogalvanic battery when being in contact with the skin. The second element 2 in the illustrated embodiment is a semiconductor element consisting of a zinc oxide coating film which is formed by baking zinc paste onto the substrate 5.

The resistance element 3 is formed by applying a coat of carbon or the like to the substrate 5 so as to connect the first and second elements 1 and 2 to each other therethrough. The resistance element has a current limiting function.

There exists a positional relationship among the first and second elements 1 and 2 and the resistance element 3 in that the first and second elements 1 and 2 are opposed to each other across the resistance element and respectively connected to both sides of the resistance element.

The first and second elements 1 and 2 and the resistance element 3 can be produced by, for example, a silk-screen printing. That is, the apparatus of the invention may be produced by forming straps of the first and second elements 1 and 2 and resistance element 3 on a raw substrate in order and cutting the raw substrate into chips of a prescribed size.

The aforesaid producing method is much the same as a method for manufacturing a chip resistor used as an electronic part. According to this method, the products can be easily produced at a low cost.

The pedestal 4 is made of an insulating material such as synthetic resin. The pedestal in the illustrated embodiment is formed in the shape of a disk. The pedestal 4 is provided in its upper surface with a fitting concave 4a for firmly fixing the first and second elements 1 and 2 and resistance element 3, which are integrated with the substrate 5. To secure the substrate 5 in the fitting concave 4a, an adhesive agent may be used.

The method for manufacturing the medical treatment apparatus mainly consists of inserting the substrate 5 having the first and second elements 1 and 2 and resistance element 3 into the fitting concave 4a and fixing the substrate by use of the adhesive agent.

The skin-contact type medical treatment apparatus described above is used by bringing the skin-contacting surface 4b of the pedestal 4 into press contact with the skin 8 at a body portion suffering stiffness or aches and securely holding the pedestal by use of adhesive cloth 7, as shown in FIG. 1 as one example.

Figure 5:
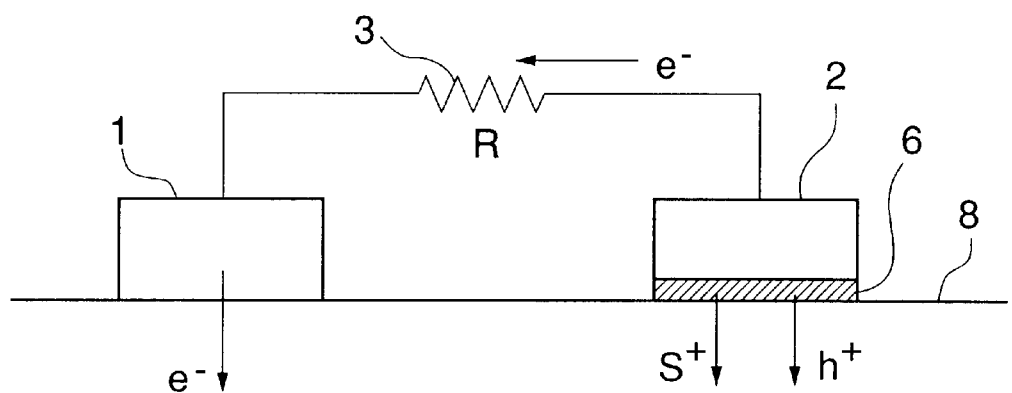
FIG. 5 is an explanatory diagram showing the operating principle of the medical treatment apparatus of the invention.
Figure 6:
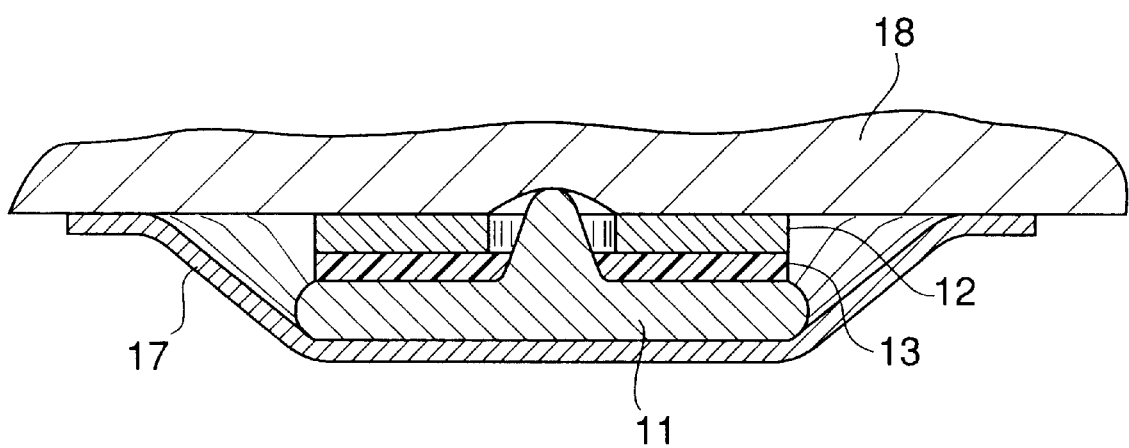
FIG. 6 is a sectional view of a conventional skin-contact type medical treatment apparatus in use.

Next, the principle of the operation of the skin-contact type medical treatment apparatus of the invention will be described with reference to FIG. 5.

Electrons $e^-$ which are emitted from the second element 2 of n-type semiconductor into the first element 1 through a resistance element 3 are injected into the skin 8, consequently bringing about a reduction effect.

On the other hand, the second element 2 of the n-type semiconductor which is lacking the electrons $e^-$ produces holes $h^+$ which concentrate in the skin due to an internal electric field of a Schottky barrier generated in the surface layer of the second element being in contact with the skin. As a result, the n-type semiconductor is ionized to allow the holes to permeate the skin 8 along with positive ions $S^+$ due to the internal electric field. Consequently, the skin undergoes an oxidizing action brought about by the holes. The oxidizing action is stably continued owing to the Schottky barrier formed in the surface layer of the second element being in contact with the skin, which functions to prevent electrons and positive ions from flowing from the skin into the second element, while generating electromotive force for a long time. Reference numeral 6 denotes a high electrical field region.

In the illustrated skin-contact type medical treatment apparatus, the first and second elements 1 and 2 and resistance element 3 are made flat, but do not overlap one another. Thus, the medical treatment apparatus of the invention is simple in structure, and therefore, it can be easily assembled by a simple operation and produced uniformly in quality and at a low cost without requiring special skills.

The materials of the first and second elements 1 and 2 are by no means limited to gold paste and zinc paste.

The thickness of the resistance element 3 in the embodiment shown in FIG. 1 is one-half the thickness of the first element 1 or second element 2, but should not be understood as being limited thereto. The thickness of the resistance element may be determined in accordance with its resistance.

Although the resistance element is used as the conductive element 3 in the foregoing embodiment, it may not always be used. The conductive element 3 may be obtained by coating conductive material such as carbon over the substrate 5. Even by such a method for forming the conductive element, the resistance of the conductive element can be determined within the range of 0 ohms to an arbitrary value so as to have a current limiting function. In other words, the resistance of the conductive element 3 may be determined to 0 ohms or more to bring about a current limiting function in accordance with the method for producing it. The conductive element 3 serves to electrically connect the first and second elements 1 and 2 to each other so as to perform the current limiting function. The conductive element 3 having a resistance of 0 ohms may be formed by using the same material as the first element 1 or second element 2 instead of the carbon coating as described above.

The pedestal 4 may not necessarily be made of synthetic resin. The pedestal formed of the insulating material includes a structure coated with the insulating material.

Although the substrate 5 is secured to the pedestal 4 by use of an adhesive agent in the aforementioned embodiment, the way of fixing the substrate is not specifically limited thereto. For example, there may be adopted a fixing method using heat, which comprises heating the substrate 5, and pressing the heated substrate onto the pedestal 4 made of synthetic resin. Consequently, the portion of the pedestal of synthetic resin, which comes into contact with the lower surface of the substrate, is melted to be mutually bonded to the substrate.

It is to be understood that the invention is not limited in its application to the details of construction and arrangement of parts illustrated in the accompanying drawings, since the invention is capable of other embodiments and of being practiced or carried out in various ways. Also it is to be understood that the phraselogy or terminology employed herein is for the purpose of description and not of limitation.

What is claimed is:

1. A skin-contact type medical treatment apparatus comprising: a first element formed of conductive metal and serving as a positive electrode, a second element formed of an n-type semiconductor and serving as a negative electrode, a pedestal made of an insulating synthetic resin material having an upper surface, and a conductive element for electrically connecting said first and second elements, said first and second elements and said conductive element being formed flat on said upper surface of said pedestal.

2. A skin-contact type medical treatment apparatus as claimed in claim 1, wherein said pedestal is provided in its upper surface with a fitting concave for securing said first and second elements and said conductive element.

3. A skin-contact type medical treatment apparatus as claimed in claim 2, wherein said first and second elements are opposed to each other across said conductive element and respectively connected to two sides of said conductive element.

4. A skin-contact type medical treatment apparatus as claimed in claim 3, wherein said conductive element is a resistance element.

5. A skin-contact type medical treatment apparatus as claimed in claim 1, wherein said first and second elements are opposed, to each other across said conductive element and respectively connected to two sides of said conductive element.

6. A skin-contact type medical treatment apparatus as claimed in claim 1, wherein said conductive element is a resistance element.

7. A skin-contact type medical treatment apparatus comprising: a first element formed of conductive metal and serving as a positive electrode, a second element formed of an n-type semiconductor and serving as a negative electrode, a pedestal made of an insulating material having an upper surface, a conductive element for electrically connecting said first and second elements, and an insulating substrate having an upper surface on which said first and second elements and said conductive element are formed, said first and second elements and said conductive element being formed flat on said upper surface of said pedestal.

8. A skin-contact type medical treatment apparatus as claimed in claim 3, wherein said pedestal is provided in its upper surface with a concave having a bottom, and said substrate is placed on said bottom of said concave in said pedestal.

9. A skin-contact type medical treatment apparatus as claimed in claim 3, wherein said substrate is made of ceramic.

10. A skin-contact type medical treatment apparatus as claimed in claim 7, wherein said conductive element is a resistance element.

11. A skin-contact type medical treatment apparatus as claimed in claim 7, wherein said first and second elements are opposed to each other across said conductive element and respectively connected to two sides of said conductive element.

12. A skin-contact type medical treatment apparatus as claimed in claim 11, wherein said conductive element is a resistance element.

13. A skin-contact type medical treatment apparatus as claimed in claim 4, wherein said substrate is made of ceramic.

14. A skin-contact type medical treatment apparatus as claimed in claim 8, wherein said conductive element is a resistance element.

15. A skin-contact type medical treatment apparatus as claimed in claim 8, wherein said first and second elements are opposed to each other across said conductive element and respectively connected to two sides of said conductive element.

16. A skin-contact type medical treatment apparatus as claimed in claim 15, wherein said conductive element is a resistance element.

17. A skin-contact type medical treatment apparatus comprising: a first element formed of conductive metal and serving as a positive electrode, a second element formed of an n-type semiconductor and serving as a negative electrode, a pedestal made of an insulating material and having an upper surface and a fitting concave in the upper surface, and a conductive element formed of a resistance element for electrically connecting said first and second elements, said first and second elements and said conductive element being formed flat on said upper surface of said pedestal and being secured in the fitting concave.

18. A skin-contact type medical treatment apparatus comprising: a first element formed of conductive metal and serving as a positive electrode, a second element formed of an n-type semiconductor and serving as a negative electrode, a pedestal made of an insulating material and having an upper surface, and a conductive element formed of a resistance element for electrically connecting at two sides thereof said first and second elements situated opposite to each other across said conductive element, said first and second elements and said conductive element being formed flat on said upper surface of said pedestal.

19. A skin-contact type medical treatment apparatus comprising a first element formed of a membrane of noble metals and serving as a positive electrode, a second element formed of an a membrane of n-type semiconductor and serving as a negative electrode, and a pedestal of synthetic resin having an upper surface, said first and second elements being electrically connected to each other through a resistance element formed into a membrane and having a voltage controlling function, said first and second elements being connected to terminal ends of said resistance element, said first and second elements and said resistance element being formed flat on said upper surface of said pedestal, said pedestal being provided in its upper surface with a concave having a bottom, and said first and second elements and said resistance element being formed on a ceramic substrate placed on said bottom of said concave in said pedestal.

* * * * *